PROCESS FOR MAKING A SILVER-GOLD ALLOY CATALYST FOR OXIDIZING ETHYLENE TO ETHYLENE OXIDE

BACKGROUND OF THE INVENTION

This invention relates to a novel method of preparing a silver catalyst and its use in the process of making ethylene oxide by the partial oxidation of ethylene in the vapor phase. Silver-containing catalysts in which the catalytically active component is the metal itself are well known in the art. An important use for the catalyst is in the direct oxidation conversion of alkenes to the corresponding vicinal epoxides, particularly in preparing ethylene oxide from ethylene by reacting ethylene with oxygen in the vapor phase.

Methods known to the art for making such catalysts include soaking a carrier or support in aqueous solutions of silver salts to impregnate it. Thereafter the thus-impregnated salts are reduced to silver metal prior to utilization in the process for oxidizing ethylene. Reduction is normally accomplished by heating in the presence of a reducing agent or by thermal decomposition of the salt. This is done at temperatures within the range of 125° C. to 400° C. and preferably from 200° C. to 300° C. Alternatively, the silver salt may be deposited from a slurry. Either slurry or solution also may contain a reducing agent, or the reducing agent may be subsequently applied.

The commonly used reducing agents are organic compounds which include polyhydric alcohols, such as liquid glycols (e.g. ethylene, propylene, and butylene glycols), glycerol, aqueous sugar solutions, aqueous polyvinyl alcohol solutions, the polyglycols, (e.g. polyethylene and polypropylene glycols) preferably of relatively low molecular weight; also included are aqueous solutions of such polyglycols, the water soluble glycol alkyl ethers, and the like.

One of the criteria for commercially useful silver catalysts is that the silver be finely divided and relatively homogeneously dispersed on the catalyst support. To obtain such finely divided silver various methods have been suggested by the prior art. In U.S. Pat. No. 2,404,438 certain carboxylic acid salts of silver are taught as useful in preparing a finely divided particulate silver for a supported catalyst.

Representative silver salts which may be employed are silver salts of certain inorganic acids for example, silver nitrate, silver chlorate, and silver metaborate, or salts of carboxylic acids such as silver acetate, slver propionate and slver formate may be used. A preferred salt is silver nitrate because it is readily soluble in aqueous solution and easily reduced, either thermally or with an organic reducing agent or hydrogen.

Supports known to be useful for making silver catalysts are for example α-alumina, zirconia, corundum, mullite, silicon carbide and carbon. α-alumina is preferred and especially a porous alumina of low surface area, i.e. less than one square meter per gram.

While silver is the metal most useful from a commercial standpoint in providing the catalytic effect necessary to obtain ethylene oxide, most commercial catalysts additionally contain small amounts of a promoter. The amount employed is usually from a few parts per million up to one or two percent, based on the weight of the total catalyst. Representative promoters include the alkali and alkaline earth metals which are usually present as their oxides. Other metals known to be promoters for the silver catalyst for the oxidation of olefins to their oxides are platinum, palladium and gold. Still others taught by the art are copper, mercury, tin, nickel and iron. Among the patents which teach gold as a promoter are included U.S. Pat. Nos. 3,773,693 and 3,844,981.

A common way of applying the promoters is to add them as their salts to the solution of the silver salt which is applied to the suport which on subsequent heating are converted to their oxides.

Other ways known to the art of adding the promoter compound are to add it to the support prior to or subsequent to the application of the silver salt. In each case the particular salt applied is dried prior to applying the solution of the second salt. Generally the promoters, when applied first, are converted to their oxides and the silver salt when applied first, is reduced to silver.

The use of a promoter in the form of an alloy is taught in U.S. Pat. No. 2,143,371 wherein gold, copper and iron are alloyed with silver. In U.S. Pat. No. 3,962,285 rhenium, ruthenium and palladium are taught as useful combinations with silver in alloy form and are described as "comprising a bulk phase of substantially pure silver and a surface alloy phase of silver and said promoter metal."

The present invention differs from the known art in that a gold salt is applied to the catalyst first and subsequently reduced to the metal, after which the silver salt is applied and then reduced. This provides a purer alloy which will contain little or no chlorides or other anions which could act as catalyst poisons. The present catalyst is more selective for ethylene oxide and is more resistant to sintering, i.e. the small particles of the catalyst remain dispersed and do not readily migrate to form larger agglomerates.

SUMMARY OF THE INVENTION

The present invention is a method of preparing an alloy of gold and silver which provides an improved catalyst for making ethylene oxide via vapor phase oxidation of ethylene. A gold salt is applied first to a suitable support and subsequently reduced to the pure metal. A silver salt is then applied which is subsequently reduced to silver, after which diffusion of gold into the silver takes place to form the homogeneous alloy.

DETAILED DESCRIPTION OF THE INVENTION

In the present method of producing a gold-silver alloy as a catalyst for ethylene oxide, gold is impregnated first, then reduced in hydrogen at 500° C. These vigorous conditions lead to the complete removal of chlorine as HCl. After cooling and washing with water the catalyst is then impregnated with an aqueous solution or despersion of a silver salt. The silver salt may then be reduced by any common methods, after which the alloy forms. One theory is that the gold crystallites act as nucleation centers for the silver, and the alloy is then formed by diffusion of the gold along the grain boundaries of the silver crystallites. Formation of the alloy may occur during the catalyst preparation or during the first week of catalyst usage.

The catalyst supports useful in the practice of the invention include α-alumina, corundum, silica and zirconia with alumina being the preferred support. In depositing the gold on the support, gold salts such as the iodide, bromide and cyanide and others having volatile

United States Patent [19]

Winterton

[11] 4,366,092

[45] Dec. 28, 1982

[54] PROCESS FOR MAKING A SILVER-GOLD ALLOY CATALYST FOR OXIDIZING ETHYLENE TO ETHYLENE OXIDE

[75] Inventor: Richard C. Winterton, Midland, Mich.

[73] Assignee: The Dow Chemical Company, Midland, Mich.

[21] Appl. No.: 288,969

[22] Filed: Jul. 31, 1981

[51] Int. Cl.$^3$ .......................... B01J 23/50; B01J 23/52
[52] U.S. Cl. ..................................... 252/476; 549/536
[58] Field of Search .............................. 252/463, 476; 260/384.34

[56] References Cited

U.S. PATENT DOCUMENTS 2,920,052  1/1960  Martin ................................. 252/463
3,773,693  11/1973  Calcagno et al. ............... 252/476 X
3,962,285  6/1976  Cusumano ...................... 252/476 X Primary Examiner—W. J. Shine
Attorney, Agent, or Firm—A. C. Ancona

[57] ABSTRACT

A method of preparing a supported catalyst of a gold-silver alloy useful for making ethylene oxide by applying a gold salt to a suitable support, reducing it to gold metal, then applying a silver salt and reducing it to silver, thereby forming a gold-silver alloy by diffusion, on the support.

5 Claims, No Drawings

UNITED STATES PATENT AND TRADEMARK OFFICE
CERTIFICATE OF CORRECTION

PATENT NO. : 4,366,092
DATED : December 28, 1982
INVENTOR(S) : Richard C. Winterton It is certified that error appears in the above—identified patent and that said Letters Patent is hereby corrected as shown below:

Col. 1, line 50; "slver" should read --silver--.
Col. 1, line 51; "slver" should read --silver--.
Col. 2, line 9; "suport" should read --support--.
Col. 2, line 56; "despersion" should read --dispersion--
Col. 2, line 62; delete the word "the".
Col. 3, line 32; "0.4%" should read --0.45%--.
Col. 4, line 34; "AU" should read --Au--.
Col. 4, line 1 of Claim 5; "1.0%" should read --0.1%--.

Signed and Sealed this

Fifth Day of July 1983

[SEAL]

Attest:

GERALD J. MOSSINGHOFF

Attesting Officer  Commissioner of Patents and Trademarks